United States Patent
Kraft

(10) Patent No.: US 8,445,424 B2
(45) Date of Patent: May 21, 2013

(54) FRAGRANCE

(75) Inventor: Philip Kraft, Dubendorf (DE)

(73) Assignee: Givaudan SA, Vernier (CH)

( * ) Notice: Subject to any disclaimer, the term of this patent is extended or adjusted under 35 U.S.C. 154(b) by 79 days.

(21) Appl. No.: 12/989,154

(22) PCT Filed: Apr. 23, 2009

(86) PCT No.: PCT/CH2009/000134
§ 371 (c)(1),
(2), (4) Date: Oct. 22, 2010

(87) PCT Pub. No.: WO2009/129643
PCT Pub. Date: Oct. 29, 2009

(65) Prior Publication Data
US 2011/0039755 A1    Feb. 17, 2011

(30) Foreign Application Priority Data

Apr. 25, 2008  (GB) ................... 0807484.1

(51) Int. Cl.
*A61Q 13/00*    (2006.01)
(52) U.S. Cl.
USPC .......................................................... 512/18
(58) Field of Classification Search
USPC .......................................................... 512/18
See application file for complete search history.

(56) References Cited

U.S. PATENT DOCUMENTS

| 3,296,080 A | 1/1967 | Meuly |
| 3,480,677 A | 11/1969 | Meuly et al. |
| 4,524,020 A | 6/1985 | Sprecker et al. |

FOREIGN PATENT DOCUMENTS

| JP | 2007077226 A | 3/2007 |
| NL | 6409113 A | 2/1965 |
| WO | 2008055704 A1 | 5/2008 |

OTHER PUBLICATIONS

XP002549041 Thomson Scientific, London, GB; AN 2007-393084 Database WPI Week 200737.
Design and Synthesis of Violet Odorants with Bicyclo[6.4.0]dodecene and Bicyclo[5.4.0]undecene Skeletons, Philip Kraft, Givaudan Roure Fragrance Research Ltd., Synthesis 1999, No. 4, pp. 695-703, Thieme Stuttgart, New York.
Design, Synthesis and Olfactory Properties of 2-Substituted 2-tert-Butyl-5-methyl-2,5-dihydrofurans: seco-Derivatives of Theaspiranes, Philip Kraft et al., Givausan Schweiz, Synthesis 2005, No. 16, pp. 2798-2809, Advanced Online Publication 2005, Georg Thieme Verlag Stuttgart, New York.
Musk or Violet? Design, Synthesis and Odor of Seco-derivates of a Musky Carotol Lead, Philip Kraft et al., Givaudan Schweiz, www.sciencedirect.com, Tetrahedron 62, 2006, 12211-12219.
English Language Abstract for JP2007077226 taken from esp@cenet.com.

*Primary Examiner* — Ling Choi
*Assistant Examiner* — Lanee Reuther
(74) *Attorney, Agent, or Firm* — Norris McLaughlin & Marcus PA

(57) ABSTRACT

A method of providing to a fragrance application a musky odor, comprising the addition thereto of at least one compound according to the formula I

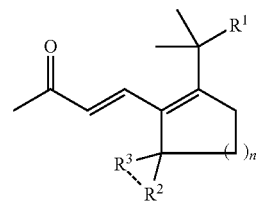

in which
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 2, 3, and 4.
The compounds are useful in the complete range of fine and functional fragrance applications.

13 Claims, No Drawings

FRAGRANCE

This application is based on PCT/CH2009/000134, which in turn claims priority from UK patent application 0807484.1 filed on 25, Apr. 2008.

This disclosure relates to dienone compounds and to their use in fragrance applications.

Musky odours have always been desired in fragrances and there is always interest in new ones to create a unique sillage, the scented wake a perfume wearer leaves behind. And really unique sillage can only be created by new musk odorants with new and uncommon side notes that extend the usual olfactory range of the musk family. Consequently, new musk odorants of uncommon tonality and character are much sought after, especially if these are in the fruity or floral direction, since fruity and floral notes are ubiquitously used in heart notes of perfumes. It has now been found that certain dienone compounds surprisingly possess this desirable fragrance characteristic. The disclosure therefore provides a method of providing to a fragrance application a musky odour, comprising the addition thereto of at least one compound according to the formula I

I in which
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 2, 3, and 4.

There is additionally provided a musky fragrance composition, said musky odour being derived at least partially from the presence therein of at least one compound of the formula I.

There is additionally provided a fragrance application having a musky odour character, comprising at least one musk-odoured compound of the formula I and at least one additional fragrance application material.

Some compounds of the formula I are known, and have been suggested for use in fragrance applications. For example, U.S. Pat. No. 3,480,677 provides novel ionones, stated to be useful as odorants in perfume compositions. However, none of these is reported to provide desirable musky odours.

By 'fragrance application' is meant any composition for any use in which the presence of fragrant substances is required. These range from fine fragrances for personal use to fragrances added to commercial cosmetic, personal and household products, such as creams and lotions, soaps and shampoos, detergent powders, fabric softeners, surface cleaners and the like.

In a particular embodiment n=1.
In particular individual embodiments:
$R^1$, $R^2$ and $R^3$=Me and n=1 (4-(2'-tert-butyl-5',5'-dimethyl-cyclopent-1'-enyl)but-3-en-2-one);
$R^1$=H, $R^2$ and $R^3$=Me and n=1 (4-(2'-isopropyl-5',5'-dimethylcyclopent-1'-enyl)but-3-en-2-one);
$R^1$=H, $R^2$ and $R^3$=Me and n=2 (4-(2'-isopropyl-6',6'-dimethylcyclohex-1'-enyl)but-3-en-2-one);
$R^1$=H, $R^2$ and $R^3$ together form a single bond and n=4 (4-(5'-isopropylspiro[2.7]dec-4'-en-4'-yl)but-3-en-2-one).

Some of the compounds of formula I are novel. There is therefore also provided a compound of the formula I, such that
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 2, 3, and 4;
with the proviso that, when $R^1$ is H and $R^2$ and $R^3$ are each Me, n is selected from 1, 3 and 4.

In a particular embodiment, n=1.
In individual particular embodiments, $R^1$, $R^2$, $R^3$ and n are selected according to one of the following possibilities:
$R^1$, $R^2$ and $R^3$=Me and n=1 (4-(2'-tert-butyl-5',5'-dimethyl-cyclopent-1'-enyl)but-3-en-2-one);
$R^1$=H, $R^2$ and $R^3$=Me and n=1 (4-(2'-isopropyl-5',5'-dimethylcyclopent-1'-enyl)but-3-en-2-one).

The compounds of formula I may be used alone or blended with one or more of the many fragrance ingredients known to the art and readily available commercially from the major fragrance manufacturers. Non-limiting examples of such ingredients include
- ethereal oils and extracts, e.g. castoreum, costus root oil, oak moss absolute, geranium oil, jasmine absolute, patchouli oil, rose oil, sandalwood oil or ylang-ylang oil;
- alcohols, e.g. citronellol, Ebanol™, eugenol, geraniol, Super Muguet™, linalool, phenylethyl alcohol, Sandalore™, terpineol or Timberol™;
- aldehydes and ketones, e.g. Azurone™, α-amylcinnamaldehyde, Georgywood™, hydroxycitronellal, Iso E Super™, Isoraldeine™, Hedione™, maltol, methyl cedryl ketone, methyl ionone or vanillin;
- ether and acetals, e.g. Ambrox™, geranyl methyl ether, rose oxide or Spirambrene™;
- esters and lactones, e.g. benzyl acetate, cedryl acetate, γ-decalactone, Helvetolide™, Serenolide™, γ-undecalactone or vetivenyl acetate;
- macrocycles, e.g. ambrettolide, ethylene brassylate or Exaltolide™; and
- heterocycles, e.g. isobutylchinoline.

In addition to their admixture with other fragrances, the compounds of the present invention may be admixed with one or more ingredients or excipients conventionally used in conjunction with fragrances in perfume compositions, for example carrier materials, and other auxiliary agents commonly used in the art, e.g., solvents such as dipropylene glycol (DPG), isopropyl myristate (IPM), and triethyl citrate (TEC).

The compounds disclosed herein may be used in a broad range of fragrance applications, for example, in any field of fine and functional perfumery, such as perfumes, household products, laundry products, body care products and cosmetics. Specific exemplary and non-limiting examples include as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant.

The compounds of formula I may conveniently be prepared from the correspondingly alkylated cycloalkanones by alkyne Grignard reactions according to Kraft, Popaj and Abate (*Synthesis* 2005, 2798-2809) by either employing but-3-yn-2-ol directly, or by using a stepwise procedure consisting of treatment of the cycloalkanones with acetylene magnesium bromide, transformation of the products into the corresponding Grignard reagents, and reaction of these with acetaldehyde. Dehydration of the resulting alkynediols, and (E)-selective hydrogenation of the triple bond with lithium aluminium hydride according to Kraft and Popaj (*Tetrahedron* 2006, 12211-12219), followed by an oxidation of the resulting allylic alcohol with pyridinium chlorochromate then provides the target compounds of formula I. The (spiro[2.(4-7)]alk-4'-en-4'-yl)but-3-en-2-ones of formula I can be prepared accordingly starting from the corresponding 5-alkyl spiro[2.(n-3)]alkan-4-ones, which are accessible for instance by spiroannulation of cycloalkanones with 2-chloroethyl methyl sulfonium iodide as outlined by Kraft (*Synthesis* 1999, 695-703), followed by subsequent alkylation in the 5-position.

The compounds can be employed in widely varying amounts, depending upon the specific application and on the nature and quantity of other fragrances. The proportions in which the compounds of the present invention are employed in application may vary within a large range of values and will depend upon the nature of the applications one intends to perfume, for example the nature of co-ingredients, and the particular effect that the perfumer seeks. Generally however, one may employ up to about 30% by weight in fine fragrances, e.g. from about 1% by weight to about 10% by weight, and up to about 40% by weight based on the perfume composition in other fragrance applications, e.g. laundry products. However, these values are given only by way of example, since the experienced perfumer may also achieve effects or may create novel accords with lower or higher concentrations.

In the formulation of fragrance applications, there may also be used any of the known ingredients used in such applications, non-limiting examples including surfactants, solvents, pigments, dyestuffs, extenders, thickeners, rheology modifiers and the like.

The compounds of formula I may be employed into the fragrance application simply by directly mixing the perfume composition with a consumer product base, i.e., a combination of all of the other ingredients needed to make the desired product. Alternatively, the compounds may be used in entrapped form, in one or more of the available entrapment materials such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzymes, or the like, and then mixed with the application. The combination of the fragrance application ingredients, including those of formula I, may be in any desired order using any known method.

There is therefore also provided a method for improving, enhancing or modifying the musk odour of a fragrance application, comprising the addition thereto of an olfactorily-acceptable amount of a compound of formula I, or a mixture thereof.

There is further provided a fragrance application comprising:
a) as musk odorant a compound of formula I or a mixture thereof; and
b) a consumer product base.

The disclosure will now be further described with reference to the following non-limiting examples. These examples are for the purpose of illustration only and it is understood that a person skilled in the art can make variations and modifications. The NMR data are given relative to internal SiMe$_4$ standard.

EXAMPLE 1

4-(2'-tert-Butyl-5',5'-dimethylcyclopent-1'-enyl)but-3-en-2-one

A solution of 2,2-dimethylcyclopentanone (10.1 g, 90.0 mmol) in THF (200 ml) was added at −70° C. within 30 min to a stirred solution of lithium diisopropylamide (2 M in THF, 45.0 ml, 90.0 mmol). After 15 min of stirring at −70° C., chlorotrimethylsilane (19.6 g, 180 mmol) was added dropwise over a period of 10 min. The reaction mixture was allowed to warm to 0° C., stirred for 1 h at this temperature and 2 h at room temp. The formed suspension was filtered off by suction with the aid of a sintered funnel and washed with Et$_2$O (100 ml), and the filtrate was concentrated under reduced pressure. Then, a solution of titanium tetrachloride (17.1 g, 90 mmol) in CH$_2$Cl$_2$ (30 ml) was added within 10 min at −60° C. to a solution of the obtained silyl enol ether (16.8 g, 88.9 mm0l) and 2-chloro-2-methylpropane (8.80 g, 95.0 mmol) in CH$_2$Cl$_2$ (200 ml). After stifling for further 30 min at −60° C., the reaction mixture was allowed to warm up to 0° C., quenched with H$_2$O (500 ml) and extracted with Et$_2$O (3×400 ml). The combined organic extracts were washed with 10% aq. NaHCO$_3$ solution (2×150 ml) and brine (2×100 ml), dried (Na$_2$SO$_4$), and the solvent was evaporated on a rotary evaporator. The resulting residue was purified by silica gel FC (pentane/Et$_2$O, 98:2, R$_f$=0.27) to provide 5-tert-butyl-2,2-dimethylcyclopentanone (13.8 g, 91%) as a colourless liquid. IR (neat): ν=1722 (s, ν$_{C=O}$), 1463 [m, δ$_{as}$(CH$_3$)], 1361 [m, δ$_s$(CH$_3$)] cm$^{-1}$. $^1$H NMR (CDCl$_3$): δ=0.92/1.05 (2s, 6 H, 2-Me$_2$), 0.99 (s, 9 H, 1'-Me$_3$), 1.51-1.59 (m, 1 H, 5-H), 1.64-1.80 (m, 2 H, 3-H$_{ax}$, 4-H$_{ax}$), 1.92-2.15 (m, 2 H, 3-H$_{eq}$, 4-H$_{eq}$) ppm. $^{13}$C NMR (CDCl$_3$): δ=22.3 (t, C-4), 23.0/24.8 (2q, 2-Me$_2$), 27.8 (q, 1'-Me$_3$), 32.3 (s, C-1'), 35.8 (t, C-3), 45.7 (s, C-2), 223.5 (s, C-1) ppm. MS (EI): m/z (%)=168 (24) [M]$^+$, 153 (11) [M-CH$_3$]$^+$, 112 (100) [M-C$_4$H$_8$]$^+$, 111 (52) [M-C$_4$H$_9$]$^+$, 57 (45) [C$_4$H$_9$]$^+$.

To a stirred solution of ethyl magnesium bromide (3 M in Et$_2$O, 53.0 ml, 159 mmol) was added drop wise within 20 min a solution of 3-butyn-2-ol (5.61 g, 80.0 mmol) in THF (100 ml) and the reaction mixture was stirred for 2 h under reflux. In a separate 2-nacked round flask, was added in one dash at 0° C. a solution of 5-tert-butyl-2,2-dimethylcyclopentanone (12.3 g, 73.0 mmol) in THF (150 ml) to anhydrous cerium(III) chloride (18.0 g, 73.0 mmol), and the suspension was stirred for 4 h at room temp. The resulting viscous slurry was added than dropwise at ambient temp. to the above prepared Grignard reagent, upon which no temperature rise was observed. The reaction mixture was stirred for 2 d at 50° C., cooled down to room temp., quenched with satd. aq. NH$_4$Cl solution (400 ml) and extracted with Et$_2$O (3×500 ml). The combined organic extracts were dried (Na$_2$SO$_4$) and evaporated. Purification of the resulting residue by silica gel FC (pentane/Et$_2$O, 6:4, R$_f$ 0.26) furnished 1-(3'-hydroxybut-1'-ynyl)-5-tert-butyl-2,2-dimethylcyclopentanol (10.6 g, 61%) as slightly yellowish oil. IR (neat): nu(tilde)=3301 (m, ν$_{O-H}$), 1465 [m, δ$_{as}$(CH$_3$)], 1366 [m, δ$_s$(CH$_3$)], 1078 (s, ν$_{C-O}$) cm$^{-1}$. $^1$H NMR (CDCl$_3$): δ=1.01/1.03 (2s, 6 H, 2-Me$_2$), 1.07 (s, 9 H, 1"-Me$_3$), 1.44 (d, J=6.5 Hz, 3 H, 4'-H$_3$), 1.65-1.70 (m, 2 H, 3-, 4-H$_b$), 1.72-1.78 (m, 2 H, 3-, 4-H$_a$), 2.10-2.14 (m, 1 H, 5-H), 2.16 (br. s, 2 H, OH), 4.56 (q, J=6.5 Hz, 1 H, 3'-H), ppm. $^{13}$C NMR (CDCl$_3$): δ=21.5/26.9 (2q, 2-Me$_2$), 22.9/23.0 (2t, C-4), 24.3/24.4 (2q, C-4'), 29.5/29.5 (2q, 1''-Me$_3$), 33.7/33.7 (2s, C-1''), 35.7/35.7 (2t, C-3), 48.4/48.5 (2s, C-2), 55.6/55.7 (2d, C-5), 58.4/58.4 (2d, C-3'), 81.5/81.5 (2s, C-1), 86.7/86.8 (s, C-1'), 87.8/87.8 (2s, C-2') ppm. MS (EI): m/z (%)=223 (2) [M-CH$_3$]$^+$, 205 (15) [M-CH$_3$—H$_2$O]$^+$, 187 (2) [M-CH$_3$—H$_2$O—H$_2$O]$^+$, 181 (12) [M-C$_4$H$_9$]$^+$, 164 (59) [M-H$_2$O—C$_4$H$_8$]$^+$, 149 (51) [M-H$_2$O—C$_5$H$_{11}$]$^+$, 121 (40)/107 (71)/93 (24)/79 (36) [C$_n$H$_{(2n-5)}$]$^+$, 57 (95) [C$_4$H$_9$]$^+$, 45 (8) [C$_2$H$_5$O]$^+$, 43 (100) [C$_2$H$_3$O]$^+$.

A solution of 1-(3'-hydroxybut-1'-ynyl)-5-tert-butyl-2,2-dimethylcyclopentanol (6.20 g, 26.0 mmol) in THF (25 ml) was added within 5 min at 0° C. to 20% aq. H$_2$SO$_4$ solution (200 ml) and THF (175 ml). After 2 h stirring at 0° C. the reaction mixture was extracted with Et$_2$O (3×250 ml). The combined organic extracts were washed with satd. aq. NaHCO$_3$ solution (2×250 ml), with brine (2×150 ml), dried (Na$_2$SO$_4$), and the solvent was evaporated on a rotary evaporator. The resulting residue was purified by silica gel FC (pentane/Et$_2$O, 95:5, R$_f$=0.16) to provide the title compound 4-(2'-tert-butyl-5',5'-dimethylcyclopent-P-enyl)but-3-yn-2-ol (2.75 g, 48%) as a colourless oil. IR (neat): v=3321 (m, v$_{O—H}$), 2150 (w, δ$_{C≡C-C}$), 1457 [m, δ$_{as}$(CH$_3$)], 1360 [m, δ$_s$(CH$_3$)] 1087 (s, v$_{C—O}$) cm$^{-1}$. $^1$H NMR (CDCl$_3$): δ=1.04 (s, 6 H, 5'-Me$_2$), 1.19 (s, 9 H, 1''-Me$_3$), 1.49 (d, J=6.5 Hz, 3 H, 1-H$_3$), 1.61 (t, J=7.5 Hz, 2 H, 4'-H$_2$), 1.93 (br. s, 1 H, OH), 2.40 (d, J=7.0 Hz, 2H, 3'-H$_2$), 4.70 (q, J=6.5 Hz, 1 H, 2-H) ppm. $^{13}$C NMR (CDCl$_3$): δ=24.4 (q, C-1), 26.8/26.9 (2q 5'-Me$_2$), 29.4 (q, 1''-Me$_3$), 31.8 (t, C-3'), 34.0 (s, C-1''), 38.0 (t, C-4'), 47.0 (s, C-5'), 59.1 (d, C-2), 81.3 (s, C-3), 96.9 (s, C-4), 124.6 (s, C-1'), 156.1 (s, C-2') ppm. MS (EI): m/z (%)=220 (53) [M]$^+$, 205 (87) [M-CH$_3$]$^+$, 187 (36) [M-CH$_4$O]$^+$, 163 (28) [M-C$_4$H$_9$]$^+$, 57 (34) [C$_4$H$_6$]$^+$, 43 (100) [C$_3$H$_7$O]$^+$.

To a stirred suspension of lithium aluminium hydride (350 mg, 9.22 mmol) in THF (5.0 ml) was added dropwise at room temp., a solution of 4-(2'-tert-butyl-5',5'-dimethylcyclopent-F-enyl)but-3-yn-2-ol (2.20 g, 10.0 mmol) in THF (20 ml), and the reaction mixture was stirred for additional 4 h at room temp. Under cooling with an ice-bath, water was added dropwise (0.35 ml), followed by 15% aq. NaOH solution (0.35 ml) and again water (1.05 ml). After stirring for further 30 min at room temp., the formed precipitate was filtered off by suction with the aid of a sintered funnel, and washed with Et$_2$O (30 ml). The combined filtrates were evaporated under reduced pressure and the resulting residue was purified by silica gel FC (pentane/Et$_2$O, 9:1, R$_f$=0.22) to provide (E)-4-(2'-tert-butyl-5',5'-dimethylcyclopent-1'-enyl)but-3-en-2-ol (1.94 g, 87%). IR (neat): v=3331 (m, v$_{O—H}$), 1457 [m, δ$_{as}$(CH$_3$)], 1360 [m, δ$_s$(CH$_3$)], 1065 (s, v$_{C—O}$), 968 (s, δ$_{C=C—H}$) cm$^{-1}$. $^1$H NMR (CDCl$_3$): δ=1.02/1.03 (2s, 6 H, 5'-Me$_2$), 1.11 (s, 9 H, 1''-Me$_3$), 1.31 (d, J=6.5 Hz, 3-H. 1-H$_3$), 1.56 (t, J=7.0 Hz, 2H, 4'-H$_2$), 2.32 (t, J=7.0 Hz, 2 H, 3'-H$_2$), 4.33-4.35 (m, 1 H, 2-H), 5.54 (dd, J=16.0, 6.5 Hz, 1 H, 3-H), 6.30 (d, J=16.0 Hz, 1 H, 4-H) ppm. $^{13}$C NMR (CDCl$_3$): δ=23.2 (q, C-1), 27.2 (q, 5'-Me$_2$), 30.7 (q, 1''-Me$_3$), 31.4 (t, C-3'), 33.7 (s, C-1''), 39.8 (t, C-4'), 47.9 (s, C-5'), 69.7 (d, C-2), 126.1 (d, C-3), 134.3 (d, C-4), 139.0 (s, C-1'), 146.1 (s, C-2') ppm. MS (EI): m/z (%)=222 (15) [M]$^+$, 207 (38) [M-CH$_3$]$^+$, 189 (83) [M-CH$_4$O]$^+$, 165 (8) [M-C$_4$H$_9$]$^+$, 133 (100) [C$_{12}$H$_{15}$]$^+$, 57 (87) [C$_4$H$_9$]$^+$, 45 (19) [C$_2$H$_5$O]$^+$, 43 (90) [C$_2$H$_3$O]$^+$.

At room temp. pyridinium chlorochromate (2.18 g, 10.1 mmol) was added portionwise to a stirred suspension of (E)-4-(2'-tert-butyl-5',5'-dimethylcyclopent-1'-enyl)but-3-en-2-ol (1.50 g, 6.75 mmol) and Celite (5.00 g) in CH$_2$Cl$_2$ (40 ml). After stirring for 5 h at ambient temp, the reaction mixture was filtered off over a pad of Celite, and washed with Et$_2$O (50 ml). The filtrate was evaporated on a rotary evaporator, and the resulting residue was purified by silica gel FC (pentane/Et$_2$O, 98:2, R$_f$=0.15) to provide the odoriferous title compound (E)-4-(2'-tert-butyl-5',5'-dimethylcyclopent-1'-enyl)but-3-en-2-one (1.34 g, 90%). IR (neat): V=1664 (s, v$_{C=O conj}$), 1459 [m, δ$_{as}$(CH$_3$)], 1360 [m, δ$_s$(CH$_3$)], 1252 (s, v$_{C=C—C=O}$), 981 (m, δ$_{C=C—H}$) cm$^{-1}$. $^1$H NMR (CDCl$_3$): δ=1.14 (s, 6 H, 5'-Me$_2$), 1.20 (s, 9 H, 1''-Me$_3$), 1.61 (t, J=7.0 Hz, 2H, 4'-H$_2$), 2.28 (s, 3 H, 1-H$_3$), 2.43 (d, J=7.0 Hz, 2 H, 3'-H$_2$), 6.16 (d, J=16.5 Hz, 1 H, 3-H), 7.37 (d, J=16.5 Hz, 1 H, 4-H) ppm. $^{13}$C NMR (CDCl$_3$): δ=26.9 (q, C-1), 27.0 (q, 5'-Me$_2$), 30.9 (q, 1''-Me$_3$), 32.5 (t, C-3'), 34.4 (s, C-1''), 40.3 (t, C-4'), 47.6 (s, C-5'), 126.6 (d, C-3), 138.7 (s, C-1'), 140.0 (d, C-4), 158.0 (s, C-2'), 199.1 (s, C-2) ppm. MS (EI): m/z (%)=220 (6) [M]$^+$, 205 (15) [M-CH$_3$]$^+$, 163 (100) [M-C$_4$H$_9$]$^+$, 57 (10) [C$_4$H$_9$]$^+$, 43 (41) [C$_2$H$_3$O]$^+$. C$_{15}$H$_{24}$O (220.4): calcd. C, 81.76; H, 10.98. found C, 81.77; H, 11.04. Odour: Powerful musk note with a typical character recalling pumpkins, beet root, dried fruits and violets.

EXAMPLE 2

4-(2'-Isopropyl-5',5'-dimethylcyclopent-1'-enyl)but-3-en-2-one

A solution of DMPU (9.86 g, 77.0 mmol) in THF (100 ml) was added at −70° C. within 5 min to a stirred solution of lithium diisopropylamide (2 M in THF, 38.5 ml, 77.0 mmol). After 10 min stirring at −70° C. a solution of 2,2-dimethylcyclopentanone (7.80 g, 70.0 mmol) in THF (50 ml) was added over a period of 30 min. The reaction mixture was warmed up to −20° C. and treated dropwise with 2-iodopropane (18.7 g, 105 mmol). The reaction mixture was warmed up slowly to room temp., stirred over night at room temp., and quenched with satd. aq. NH$_4$Cl solution (300 ml) and extracted with Et$_2$O (3×300 ml). The combined organic extracts were dried (Na$_2$SO$_4$), and concentrated under the reduced pressure. The resulting residue was purified by silica gel FC (pentane/Et$_2$O, 98:2, R$_f$ 0.25) to furnish 5-isopropyl-2,2-dimethylcyclopentanone (8.42 g, 78%). IR (neat): v=1731 (s, v$_{C=O}$), 1462 [m, δ$_{as}$(CH$_3$)], 1367 [m, δ$_s$(CH$_3$)] cm$^{-1}$. $^1$H NMR (CDCl$_3$): δ=0.80/0.99 (2d, J=7.0 Hz, 6 H, 1'-Me$_2$), 0.94/1.06 (2s, 6 H, 2-Me$_2$), 1.62-1.69 (m, 2 H, 3-H$_{ax}$, 4-H$_{ax}$), 1.76-1.81 (m, 1 H, 5-H), 1.89-1.94 (m, 1 H, 1'-H), 2.11-2.17 (m, 2 H, 3-H$_{eq}$, 4-H$_{eq}$) ppm. $^{13}$C NMR (CDCl$_3$): δ=18.4/21.1 (2q, 1'-Me$_2$), 20.6 (t, C-4), 23.1/24.7 (2q, 2-Me$_2$), 27.4 (d, C-1'), 36.4 (t, C-3), 45.3 (s, C-2), 224.1 (s, C-1) ppm. MS (EI): m/z (%)=154 (15) [M]$^+$, 139 (7) [M-CH$_3$]$^+$, 112 (36) [M-C$_3$H$_6$]$^+$, 97 (18) [M-C$_4$H$_9$]$^+$, 56 (100) [C$_3$H$_4$O]$^+$.

To a stirred solution of ethyl magnesium bromide (3 M in Et$_2$O, 35.3 ml, 106 mmol) was added dropwise within 20 min a solution of 3-butyn-2-ol (3.72 g, 53.0 mmol) in THF (80 ml) and the reaction mixture was stirred for 2 h under reflux. In a separate 2-nacked round flask, was added in one dash at 0° C. a solution of 5-isopropyl-2,2-dimethylcyclopentanone (7.40 g, 48.0 mmol) in THF (100 ml) to anhydrous cerium(III) chloride (11.8 g, 48.0 mmol), and the suspension was stirred for 4 h at room temp. The resulting viscous slurry was added than dropwise at ambient temp. to the above prepared Grignard reagent, upon which no temp. rise was observed. The reaction mixture was stirred for 2 d at 50° C., cooled down to room temp., quenched with satd. aq. NH$_4$Cl solution (300 ml) and extracted with Et$_2$O (3×400 ml). The combined organic extracts were dried (Na$_2$SO$_4$) and evaporated. Purification of the resulting residue by silica gel FC (pentane/Et$_2$O, 6:4, R$_f$ 0.23) furnished 1-(3'-hydroxybut-1'-ynyl)-5-isopropyl-2,2-dimethylcyclopentanol (7.12 g, 66%) as slightly yellowish oil. IR (neat): ν=3297 (m, ν$_{O—H}$), 1467 [m, δ$_{as}$(CH$_3$)], 1365 [m, δ$_s$(CH$_3$)], 1061 (s, ν$_{C—O}$) cm$^{-1}$. $^1$H NMR (CDCl$_3$): δ=0.91/1.04 (2d, J=6.5 Hz, 6 H, 1''-Me$_2$), 0.98/1.08 (2s, 6 H, 2-Me$_2$), 1.26-1.45 (m, 2 H, 3-H$_{ax}$, 4-H$_{ax}$), 1.45/1.47 (2d, J=6.5 Hz, 3 H, 4'-H$_3$), 1.54-1.62 (m, 1 H, 5-H), 1.69-1.84 (m, 2 H, 3-H$_{eq}$, 4-H$_{eq}$), 1.82 (br. s, 2 H, OH), 1.85-1.94 (m, 1 H, 1''-H), 2.49/2.54 (2s, 1 H, 2'-H), 4.59/4.60 (2q, J=6.5 Hz, 1 H, 3'-H), ppm. $^{13}$C NMR (CDCl$_3$): δ=21.6/21.7 (2q, 1''-Me$_2$), 22.2/22.4 (2q, 2-Me$_2$), 24.3/24.5 (2q, C-4'), 25.4/26.8 (2t, C-4), 30.1/32.3 (2d, C-1''), 35.4/35.7 (2t, C-3), 46.1/48.3 (2s, C-2), 54.0/54.1 (2d, C-5), 58.3/58.4 (2d, C-3'), 80.1/82.0 (2s, C-1), 84.3/86.4 (s, C-1'), 87.8/89.6 (2s, C-2') ppm. MS (EI): m/z (%)=224 (2) [M]$^+$, 209 (3) [M-CH$_3$]$^+$, 206 (10) [M-H$_2$O]$^+$, 191 (61) [M-C$_2$H$_5$O]$^+$, 45 (12) [C$_2$H$_5$O]$^+$.

A solution of 1-(3'-hydroxybut-1'-ynyl)-5-isopropyl-2,2-dimethylcyclopentanol (4.82 g, 21.5 mmol) in THF (20 ml) was added within 5 min at 0° C. to 20% aq. H$_2$SO$_4$ solution (150 ml) and THF (130 ml). After 2 h stirring at 0° C. the reaction mixture was extracted with Et$_2$O (3×200 ml). The combined organic extracts were washed with satd. aq. NaHCO$_3$ solution (2×200 ml), with brine (2×100 ml), dried (Na$_2$SO$_4$), and the solvent was evaporated on a rotary evaporator. The resulting residue was purified by silica gel FC (pentane/Et$_2$O, 95:5, R$_f$=0.14) to provide 4-(2'-isopropyl-5',5'-dimethylcyclopent-1'-enyl)but-3-yn-2-ol (2.27 g, 51%) as colourless oil. IR (neat): ν=3331 (m, ν$_{O—H}$), 2150 (w, δ$_{C≡C—C}$), 1455 [m, δ$_{as}$(CH$_3$)], 1360 [m, δ$_s$(CH$_3$)], 1093 (s, ν$_{C—O}$) cm$^{-1}$. $^1$H NMR (CDCl$_3$): δ=1.00 (d, J=7.0 Hz, 6 H, 1''-Me$_2$), 1.06 (s, 6 H, 5'-Me$_2$), 1.50 (d, J=6.5 Hz, 3 H, 1-H$_3$), 1.66 (t, J=7.0 Hz, 2 H, 4'-H$_2$), 1.95 (br. s, 1 H, OH), 2.30 (d, J=7.0 Hz, 2 H, 3'-H$_2$), 2.87 (sept, J=7.0 Hz, 1 H, 1''-H), 4.71 (q, J=6.5 Hz, 1 H, 2-H) ppm. $^{13}$C NMR (CDCl$_3$): δ=20.8 (q, 1''-Me$_2$), 24.8 (q, C-1), 27.0/27.1 (2q 5'-Me$_2$), 28.7 (t, C-3'), 29.1 (d, C-1''), 38.3 (t, C-4'), 46.6 (s, C-5'), 59.1 (d, C-2), 79.5 (s, C-3), 95.9 (s, C-4), 125.2 (s, C-1'), 155.2 (s, C-2') ppm. MS (EI): m/z (%)=206 (63) [M]$^+$, 191 (88) [M-CH$_3$]$^+$, 173 (23) [M-CH$_4$O]$^+$, 163 (46) [M-C$_3$H$_7$]$^+$, 45 (10) [C$_2$H$_5$O]$^+$, 43 (100) [C$_3$H$_7$]$^+$.

To a stirred suspension of lithium aluminium hydride (351 mg, 9.22 mmol) in THF (5.0 ml) was added dropwise at room temp., a solution of 4-(2'-isopropyl-5',5'-dimethylcyclopent-1'-enyl)but-3-yn-2-ol (1.91 g, 9.25 mmol) in THF (20 ml), and the reaction mixture was stirred for additional 4 h at room temp. Under cooling with an ice-bath, water was added dropwise (0.35 ml), followed by 15% aq. NaOH solution (0.35 ml) and again water (1.05 ml). After stirring for further 30 min at room temp., the formed precipitate was filtered off by suction with the aid of a sintered funnel, and washed with Et$_2$O (30 ml). The combined filtrates were evaporated under reduced pressure, and the resulting residue was purified by silica gel FC (pentane/Et$_2$O, 9:1, R$_f$=0.21) to provide (E)-4-(2'-isopropyl-5',5'-dimethylcyclopent-1'-enyl)but-3-en-2-ol (1.66 g, 86%). IR (neat): ν=3318 (m, ν$_{O—H}$), 1455 [m, δ$_{as}$(CH$_3$)], 1361 [m, δ$_s$(CH$_3$)], 1029 (s, ν$_{C—O}$), 964 (s, δ$_{C=C—H}$) cm$^{-1}$. $^1$H NMR (CDCl$_3$): δ=0.99 (d, J=7.0 Hz, 6 H, 1''-Me$_2$), 1.10/1.11 (2s, 6 H, 5'-Me$_2$), 1.31 (d, J=6.5 Hz, 3-H. 1-H$_3$), 1.60 (t, J=7.5 Hz, 2 H, 4'-H$_2$), 2.24 (t, J=7.5 Hz, 2 H, 3'-H$_2$), 2.84 (sept, J=7.0 Hz, 1 H, 1''-H), 4.34 (quint, J=6.5 Hz, 1 H, 2-H), 5.73 (dd, J=16.0, 6.5 Hz, 1H, 3-H), 6.18 (d, J=16.0 Hz, 1 H, 4-H) ppm. $^{13}$C NMR (CDCl$_3$): δ=21.3 (q, 1''-Me$_2$), 24.5 (q, C-1), 27.0 (d, C-1''), 27.1/27.2 (2q, 5'-Me$_2$), 27.8 (t, C-3'), 40.1 (t, C-4'), 46.5 (s, C-5'), 70.0 (d, C-2), 123.1 (d, C-3), 133.0 (d, C-4), 138.3 (s, C-1'), 146.8 (s, C-2') ppm. MS (EI): m/z (%)=208 (10) [M]$^+$, 193 (14) [M-CH$_3$]$^+$, 175 (40) [M-CH$_4$O]$^+$, 135 (100) [C$_{10}$H$_{15}$]$^+$, 45 (11) [C$_2$H$_5$O]$^+$, 43 (49) [C$_3$H$_7$]$^+$.

At room temp. pyridinium chlorochromate (1.97 g, 9.15 mmol) was added portionwise to a stirred suspension of (E)-4-(2'-isopropyl-5',5'-dimethylcyclopent-1'-enyl)but-3-en-2-ol (1.27 g, 6.10 mmol) and Celite (5.00 g) in CH$_2$Cl$_2$ (40 ml). After stifling for 5 h at ambient temp, the reaction mixture was filtered off over a pad of Celite, and washed with Et$_2$O (50 ml). The filtrate was evaporated on a rotary evaporator, and the resulting residue was purified by silica gel FC (pentane/Et$_2$O, 98:2, R$_f$=0.12) to provide the odoriferous title compound (E)-4-(2'-isopropyl-5',5'-dimethylcyclopent-1'-enyl)but-3-en-2-one (1.12 g, 89%). IR (neat): ν=1688 (s, ν$_{C=Oconj}$), 1458 [m, δ$_{as}$(CH$_3$)], 1360 [m, δ$_s$(CH$_3$)], 1252 (s, ν$_{C—C—C=O}$), 973 (m, δ$_{C=C—H}$) cm$^{-1}$. $^1$H NMR (CDCl$_3$): δ=1.04 (d, J=7.0 Hz, 6 H, 1''-Me$_2$), 1.18 (s, 6 H, 5'-Me$_2$), 1.67 (t, J=7.5 Hz, 2 H, 4'-H$_2$), 2.29 (s, 3 H, 1-H$_3$), 2.34 (d, J=7.5 Hz, 2 H, 3'-H$_2$), 2.99 (sept, J=7.0 Hz, 1 H, 1''-H), 6.28 (d, J=16.5 Hz, 1 H, 3-H), 7.37 (d, J=16.5 Hz, 1 H, 4-H) ppm. $^{13}$C NMR (CDCl$_3$): δ=21.2 (q, 1''-Me$_2$), 26.9 (q, 5'-Me$_2$), 27.3 (d, C-1''), 27.6 (q, C-1), 28.7 (t, C-3'), 40.2 (t, C-4'), 46.3 (s, C-5'), 125.7 (d, C-3), 136.4 (d, C-4), 138.3 (s, C-1'), 159.0 (s, C-2'), 199.0 (s, C-2) ppm. MS (EI): m/z (%)=206 (6) [M]$^+$, 191 (5) [M-CH$_3$]$^+$, 163 (100) [M-C$_2$H$_3$O]$^+$, 43 (38) [C$_3$H$_7$]$^+$. C$_{14}$H$_{22}$O (206.3): calcd. C, 81.50; H, 10.75. found C, 81.43; H, 10.70. Odour: Powerful musk note with a typical fruity-floral character recalling pumpkins, dried apples, violets and orris, in front of an elegant woody background.

EXAMPLE 3

4-(2% Isopropyl-6',6'-dimethylcyclohex-1'-enyl)but-3-en-2-one

As described in Example 3 for preparation of 5-isopropyl-2,2-dimethylcyclopentanone, from 2,2-dimethylcyclohexanone (12.6 g, 110 mmol), lithium diisopropylamide solution (2 M in THF, 55.0 ml, 110 mmol), DMPU (14.1 g, 110 mmol) and 2-iodopropane (25.5 g, 150 mmol), 6-isopropyl-2,2-dimethylcyclohexanone (13.1 g, 78%) was obtained after standard workup and purification by silica gel FC (pentane/Et$_2$O, 6:4, R$_f$=0.26).

A solution of 6-isopropyl-2,2-dimethylcyclohexanone (12.6 g, 75.0 mmol) in THF (50 ml) was added within 10 min at room temperature to a stirred solution of ethynyl magnesium bromide in THF (0.5 M, 180 ml, 90 mmol), and the reaction mixture was stirred for 2 d at 60° C. The reaction mixture was allowed to cool to room temperature, quenched with satd. aq. NH$_4$Cl solution (500 ml) and extracted with Et$_2$O (3×300 ml). The combined organic extracts were dried (Na$_2$SO$_4$) and evaporated. Purification of the resulting residue by silica gel FC (pentane/Et$_2$O, 98:2, R$_f$ 0.21) furnished 1-ethynyl-6-isopropyl-2,2-dimethylcyclohexanol (11.8 g, 81%) as a colorless liquid.

At room temp, a solution of 1-ethynyl-6-isopropyl-2,2-dimethylcyclohexanol (11.1 g, 57.0 mmol) in THF (150 ml) was added dropwise to a stirred ethyl magnesium bromide solution in ether (3 M, 38.0 ml, 114 mmol), and the resulting reaction mixture was stirred for 3 h at room temperature. A solution of acetaldehyde (2.52 g, 57.0 mmol) in THF (50 ml) was then added within 30 min, and the reaction mixture stirred overnight at room temperature. The reaction mixture was quenched with satd. aq. NH$_4$Cl solution (600 ml), and extracted with Et$_2$O (3×4000 ml). The combined organic extracts were dried (Na$_2$SO$_4$), and the solvent was evaporated on a rotary evaporator. The resulting residue was purified by silica gel FC (pentane/Et$_2$O 6:4; R$_f$ 0.25) to provide 1-(3'-hydroxybut-1'-ynyl)-6-isopropyl-2,2-dimethylcyclohexanol (11.3 g, 83%) as a slightly yellowish oil.

As described in Example 2 for the preparation of 4-(2'-isopropyl-5',5'-dimethylcyclopent-1'-enyl)but-3-yn-2-ol, from 1-(3'-hydroxybut-1'-ynyl)-6-isopropyl-2,2-dimethylcyclohexanol (5.96 g, 25.0 mmol) and 30% aq. $H_2SO_4$ solution (200 ml) in THF (200 ml), 4-(2'-isopropyl-6',6'-dimethylcyclohex-1'-enyl)but-3-yn-2-ol (1.32 g, 24%) was obtained after standard workup and purification by silica gel FC (pentane/$Et_2O$, 95:5; $R_f$ 0.15).

As described for preparation of (E)-4-(2'-isopropyl-5',5'-dimethylcyclopent-1'-enyl)but-3-en-2-ol in Example 2, (E)-4-(2'-isopropyl-6',6'-dimethylcyclohex-1'-enyl)but-3-en-2-ol (1.15 g, 92%) was obtained from 4-(2'-isopropyl-6',6'-dimethylcyclohex-1'-enyl)but-3-yn-2-ol (1.23 g, 5.60 mmol) and lithium aluminium hydride (213 mg, 5.60 mmol) in THF (15 ml), after standard workup and purification by silica gel FC (pentane/$Et_2O$, 9:1; $R_f$ 0.23).

As described for preparation of (E)-4-(2'-isopropyl-5',5'-dimethylcyclopent-1'-enyl)but-3-en-2-one, from (E)-4-(2'-isopropyl-6',6'-dimethylcyclohex-1'-enyl)but-3-en-2-ol (1.05 g, 4.70 mmol) and pyridinium chlorochromate (1.21 g, 5.60 mmol) in $CH_2Cl_2$ (30 ml), the odoriferous title compound (E)-4-(2'-isopropyl-6',6'-dimethylcyclohex-1'-enyl)but-3-en-2-one (808 mg, 78%). was obtained after standard workup and purification by silica gel FC (pentane/$Et_2O$, 98:2; $R_f$ 0.14). IR (neat): $v=1672$ (s, $v_{C=O conj}$), 1459 [m, $\delta_{as}$(CH$_3$)], 1360 [m, $\delta_s$(CH$_3$)], 1250 (s, $v_{C=C-C=O}$), 979 (m, $\delta_{C=C-H}$) cm$^{-1}$. $^1$H NMR (CDCl$_3$): $\delta=0.95$ (d, J=7.0 Hz, 6 H, 1"-Me$_2$), 1.03 (s, 6 H, 6'-Me$_2$), 1.42-1.48 (m, 2 H, 5'-H$_2$), 1.58-1.64 (m, 2 H, 4'-H$_2$), 1.97 (t, J=7.5 Hz, 2 H, 3'-H$_2$), 2.30 (s, 3 H, 1-H$_3$), 2.86 (sept, J=7.0 Hz, 1 H, 1"-H), 6.08 (d, J=16.5 Hz, 1 H, 3-H), 7.28 (d, J=16.5 Hz, 1 H, 4-H) ppm. $^{13}$C NMR (CDCl$_3$): $\delta=19.1$ (t, C-4'), 21.1 (q, 1"-Me$_2$), 23.9 (t, C-3'), 27.1 (q, C-1), 28.9 (q, 6'-Me$_2$), 30.8 (d, C-1"), 34.2 (s, C-&'), 39.6 (t, C-3'), 131.9 (d, C-3), 134.6 (s, C.-1'), 142.3 (s, C-2'), 144.3 (d, C-4) 188.2 (s, C-2) ppm. MS (EI): m/z (%)=220 (6) [M]$^+$, 205 (4) [M-CH$_3$]$^+$, 177 (100) [M-C$_2$H$_3$O]$^+$, 43 (30) [C$_3$H$_7$]$^+$. Odour: Distinct sweet musk note of characteristic fruity-floral tonality recalling dried apples and crystallized violet petals with woody-earthy notes in the background,

EXAMPLE 4

Modern Unisex Chypre Fine Fragrance

| Compound/Ingredient | parts by weight 1/1000 |
|---|---|
| Allyl amyl glycolate (pentyloxyacetic acid allyl ester) | 10 |
| Ambrofix ((3aR,5aS,9aS,9bR)-dodecahydro-3a,6,6,9a-tetramethylnaphtho[2,1-b]furan) | 2 |
| Bergamot oil Italy | 45 |
| 1-(Cyclooct-3-enyl)propan-1-ol | 45 |
| alpha-Damascone @ 10% in DPG (dipropylene glycol) | 8 |
| Dihydromyrcenol | 25 |
| Dipropylene glycol (DPG) | 242 |
| Ethyl linalool | 45 |
| 2-Ethyl-N-methyl-N-meta-tolyl butyramide | 8 |
| Ethylene brassylate (1,4-dioxacycloheptadecane-5,17-dione) | 90 |
| Florol (2-isobutyl-4-methyltetrahydro-2H-pyran-4-ol) | 45 |
| Georgywood (cis-1-(1,2,3,4,5,6,7,8-octahydro-1,2,8,8-tetramethyl-2-naphtalenyl)ethanone) | 55 |
| (3Z)-Hex-3-enyl salicylate | 30 |
| Hexyl cinnamic aldehyde | 45 |
| Iso E Super (2,3,8,8-tetramethyl-1,2,3,4,5,6,7,8-octahydro-2-naphthalenyl methyl ketone and isomers) | 55 |

-continued

| Compound/Ingredient | parts by weight 1/1000 |
|---|---|
| Jasmine absolute Egypt pure | 2 |
| Lilial (3-(4-tert-butylphenyl)-2-methylpropanal) | 45 |
| Linalool | 45 |
| Mandarin oil Italy | 15 |
| 6-Methoxy-2,6-dimethyloctanal | 10 |
| Patchouli oil Indonesia | 20 |
| (contd.) | |
| Spirogalbanone (1-spiro[4.5]dec-6/7-en-7-ylpent-4-en-1-one) @ 1% in DPG (dipropylene glycol) | 8 |
| Vanillin | 5 |
| 4-(2'-tert-Butyl-5',5'-dimethylcyclopent-1'-enyl)but-3-en-2-one | 100 |
| | 1000 |

At 10%, 4-(2'-tert-butyl-5',5'-dimethylcyclopent-1'-enyl)but-3-en-2-one provides to this fruity-floral, spicy fresh unisex composition in combination with ethylene brassylate a very typical warm, velvety signature musk note that with its aspects of dried fruits, violets, beet root and pumpkins perfectly harmonizes and extends the floral-spicy theme of the heart note. Albeit no oak moss is contained in the formula, the fragrance still satisfies the classical Chypre concept, since the 4-(2'-tert-butyl-5',5'-dimethylcyclopent-1'-enyl)but-3-en-2-one renders in combination with patchouli oil, Iso E Super and Georgywood a similar impact and long-lasting sillage. Albeit a typical Chypre fragrance, it remains modern, unique and distinct due to the unusual accents of 4-(2'-tert-butyl-5', 5'-dimethylcyclopent-1'-enyl)but-3-en-2-one.

The invention claimed is:

1. A method of providing to a fragrance application a musky odour, comprising the step of: adding to the fragrance application at least one compound according to the formula I

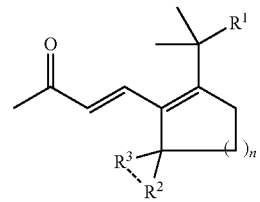

I in which $R^1$ is selected from H and $CH_3$;

$R^2$, $R^3$ are selected from the possibilities that (a) both are $CH_3$; and (b) $R^2$ and $R^3$ together form a single bond (as indicated by the broken line); and n is an integer selected from 1, 3, and 4.

2. A method according to claim 1, in which n=1.

3. A method according to claim 2, wherein the compound according to formula I, is characterized in exhibiting a beet root odor.

4. A method according to claim 2, wherein the compound 4-(2'-tert-butyl-5', 5'-dimethycyclopent-1'-enyl) but-3-en-2-one, exhibits a beet root odor.

5. A method according to claim 1, in which the compound according to formula I is:
4-(2'-tert-butyl-5', 5'-dimethylcyclopent-1'-enyl)but-3-en-2-one.

6. A method according to claim 1, wherein the compound according to formula I, is characterized in exhibiting a beet root odor.

7. A compound of the formula I

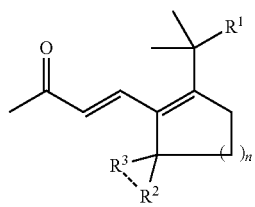

in which:
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 3, and 4;
with the proviso that, when $R^1$ is H and $R^2$ and $R^3$ are each Me, n is selected from 1, 3 and 4.

8. A compound according to claim 7, in which n=1.

9. A fragrance application having a musky odour character, said musky odour being derived at least partially from including within the fragrance application at least one compound of formula I

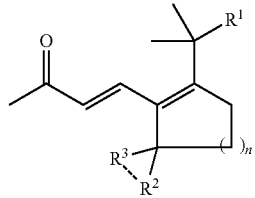

in which
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 3, and 4.

10. A fragrance application according to claim 9, in which n=1.

11. A fragrance application comprising:
a) a consumer product base; and
b) as musk odorant a compound of formula I or a mixture thereof;

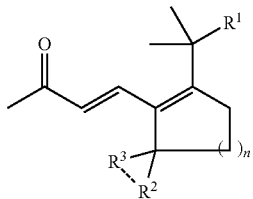

in which
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 2, 3, and 4.

12. A method for improving, enhancing or modifying the musk odour of a fragrance application, comprising the step of: adding to the fragrance application an olfactorily-acceptable amount of a compound of formula I, or a mixture thereof:

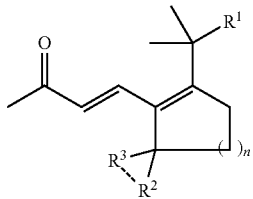

in which
$R^1$ is selected from H and $CH_3$;
$R^2$, $R^3$ are selected from the possibilities that (a) both are $CH_3$; and (b) $R^2$ and $R^3$ together form a single bond (as indicated by the broken line); and
n is an integer selected from 1, 3, and 4.

13. A method according to claim 12, in which n=1.

* * * * *